United States Patent [19]

Jacobs

[11] Patent Number: 4,539,855

[45] Date of Patent: Sep. 10, 1985

[54] APPARATUS FOR TRANSFERRING LIQUID OUT OF A CAPPED CONTAINER, AND ANALYZER UTILIZING SAME

[75] Inventor: Merrit N. Jacobs, Fairport, N.Y.

[73] Assignee: Eastman Kodak Company, Rochester, N.Y.

[21] Appl. No.: 606,489

[22] Filed: May 3, 1984

[51] Int. Cl.³ .................................. G01N 35/06
[52] U.S. Cl. ...................... 73/864.25; 141/130; 422/100
[58] Field of Search ........... 73/864.14, 864.21, 864.22, 73/864.23, 864.24, 864.25; 422/100, 63, 64, 65, 66; 141/130, 265, 281, 282

[56] References Cited

U.S. PATENT DOCUMENTS 3,992,158  11/1976  Przybylowicz et al. .
4,053,381  10/1977  Hamblen et al. .
4,258,001  3/1981   Pierce et al. .
4,287,155  9/1981   Tersteeg et al. .
4,340,390  7/1982   Collins et al. .
4,347,875  9/1982   Columbus .
4,495,149  1/1985   Iwata et al. ...................... 73/864.11

Primary Examiner—S. Clement Swisher
Attorney, Agent, or Firm—Dana M. Schmidt

[57] ABSTRACT

Apparatus is disclosed for transferring liquid out of a container covered by a pierceable cap using a storage unit. The apparatus includes means for moving the storage unit into an aspirating position within the capped container, means for aspirating the liquid into the storage unit, means for moving the storage unit away from such aspirating position, and means for dispensing at least a fraction of the liquid out of the storage unit. The apparatus further includes means for holding such container during all movement of the storage unit away from its aspirating position.

6 Claims, 9 Drawing Figures

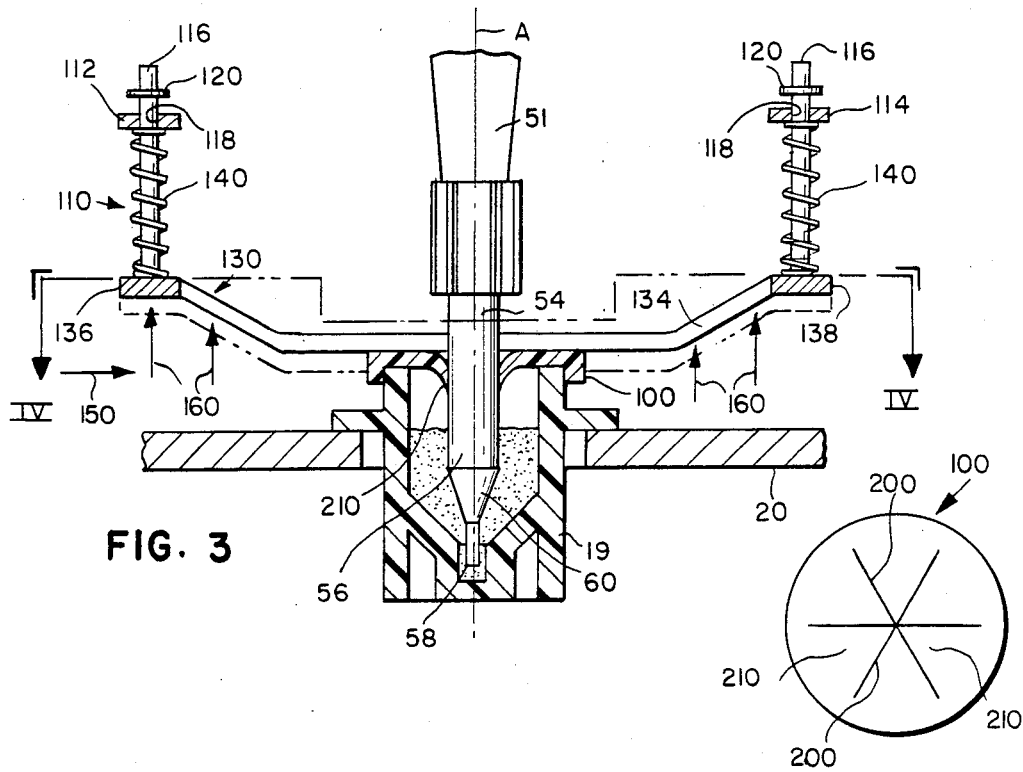
FIG. 3
FIG. 5
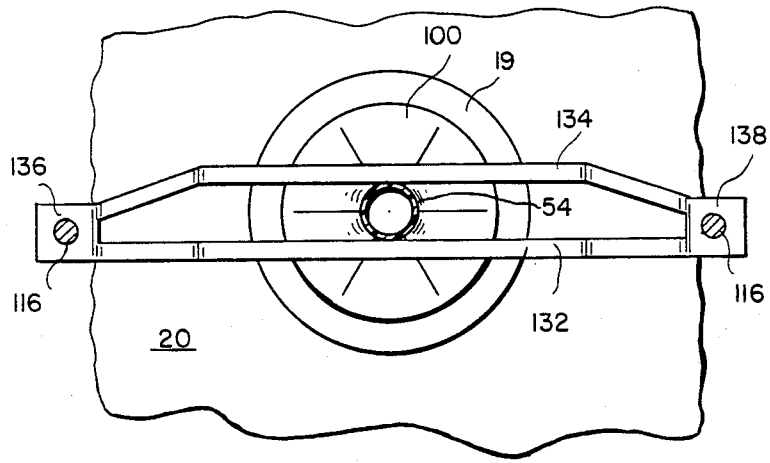
FIG. 4

APPARATUS FOR TRANSFERRING LIQUID OUT OF A CAPPED CONTAINER, AND ANALYZER UTILIZING SAME

FIELD OF THE INVENTION

This invention relates to liquid transfer apparatus, such as is used in analyzers, to transfer liquid from a capped container to analysis means.

BACKGROUND OF THE INVENTION

Analyzers have been provided for the detection of the concentration of liquid analytes using a analysis means, so-called dried test elements that contain within themselves the necessary reagents to permit such detection. Examples of such analyzers are described in U.S. Pat. Nos. 4,287,155, issued Sept. 1, 1981, and 4,340,390, issued July 20, 1982. Examples of such test elements appear in U.S. Pat. Nos. 3,992,158, issued Nov. 16, 1976; 4,053,381, issued Oct. 11, 1977; and 4,258,001, issued Mar. 24, 1981.

As is evident in the aforesaid U.S. Pat. No. 4,340,390, the preferred method of dispensing a small quantity of test liquid onto the test element is to transfer at least that quantity to be dispensed, from a first container into a temporary storage unit called a disposable tip, such as by aspiration, and then to pressurized such tip by amounts effective to dispense the small quantity of liquid onto the test element. To prevent loss of analyte and contamination, such first containers are covered by a cap designed to be pierced by the movement of the disposable tip into the container. The preferred material of the caps have been a plastic which permits teeth-like segments to be fragmented into bendable teeth during the piercing step. Because such teeth make the cap stick to the disposable tip, it has been necessary to provide means for stripping the cap and container off the disposable tip as the latter is withdrawn from the aspirating position within the liquid of the container.

Prior to this invention, such stripping means have been a fixed surface that encounters the cap after some movement of the tip has already occurred away from the aspirating position. As a result, stripping does not occur until the container has been lifted off its surface. I have discovered that this produces a final separation of cap and tip wherein the container and cap actually fall away from the tip under the influence of gravity, at a rate that is an order of magnitude greater than the nominal rate of movement of the tip.

A significant problem in the metering of liquid from such disposable tips has been that of perfusion. "Perfusion" is defined herein to mean movement of the liquid being dispensed, up the exterior surface of the tip rather than down onto the test element. As will be readily apparent, perfusion is totally unsatisfactory, as it renders unlikely that the desired amount, or indeed any amount, of liquid will be dispensed onto the test element. Considerable attempts have been made to reduce the tendency of dispensed liquid to perfuse. For example, the dispensing end of the disposable tip has been especially shaped and coated with a surfactant, as described for example in U.S. Pat. No. 4,347,875, issued on Sept. 7, 1982, to discourage the formation during aspiration of exterior liquid such as would be likely to encourage perfusion during subsequent dispensing. However, even such approaches, although very useful in reducing the number of perfusions, have not been totally successful.

SUMMARY OF THE INVENTION

This invention is based partly upon the discovery that at least some of the perfusion occurrences appear to be due to the increase in withdrawal rate of the dispensing end of the disposable tip from the liquid that occurs when the cap and container fall off during the aforedescribed stripping operation. In this invention, an analyzer is provided wherein the stripping is modified to reduce the rate of separation of the disposable tip from the container.

More specifically, there is provided apparatus for transferring liquid from a container covered by a pierceable cap, to analysis means for analyzing such liquid. The apparatus includes means for aspirating such liquid from the container into a storage unit constructed to receive and dispense such liquid, means for moving the unit: (i) from a location outside of the container, into an aspirating position in which such cap is pierced by such storage unit and the unit is immersed in the liquid in such container, and (ii) away from the aspirating position. The apparatus also includes stripping means for stripping the pierced cap off the storage unit, and means for dispensing at least a fraction of such liquid out of the storage unit onto such analysis means. The apparatus is improved in that the stripping means includes means for holding such container during the entire movement of the storage unit away from the aspirating position therein, to prevent non-uniform relative movement between the storage unit and the container. Rapid increases in withdrawal rate and the resulting perfusion during subsequent dispensing are therefore reduced.

Such improved apparatus is particularly useful as part of analyzer apparatus for measuring the concentration of the analytes of the liquid.

Thus, it is advantageous feature of the invention that apparatus such as a clinical analyzer is provided for transferring liquid from a capped container to a disposable tip in a manner that reduces the tendency of perfusion of liquid dispensed from the tip.

Other advantageous features will become apparent upon reference to the following Detailed Description of the Preferred Embodiments, when read in light of the attached drawings.

BRIEF DESCRIPTION OF THE DRAWINGS

FIG. 3 is a fragmentary sectional view in elevation showing the apparatus in its aspirating mode;

FIG. 4 is a fragmentary sectional view taken along the line IV—IV of FIG. 3;

FIG. 5 is a plan view of the cap used with the containers and which is affected by the stripper of this invention;

DETAILED DESCRIPTION OF THE PREFERRED EMBODIMENTS

The invention is particularly useful in, and this description particularly recites, a clinical analyzer used to conduct colorimetric and potentiometric assays using the dried test elements noted in the patents set forth above. This description is most particularly directed to use in analyzers which feature a disposable tip as the storage unit for dispensing aspirated liquid. In addition, the invention is useful in other apparatus wherein liquid to be analyzed is transferred from a capped container to a storage unit that penetrates the cap of the container.

Terms such as "up", "down", "lower", "vertical", "horizontal", and "bottom", as used herein refer to the orientation of parts when the apparatus is positioned in its customary position of use.

Figure 1:
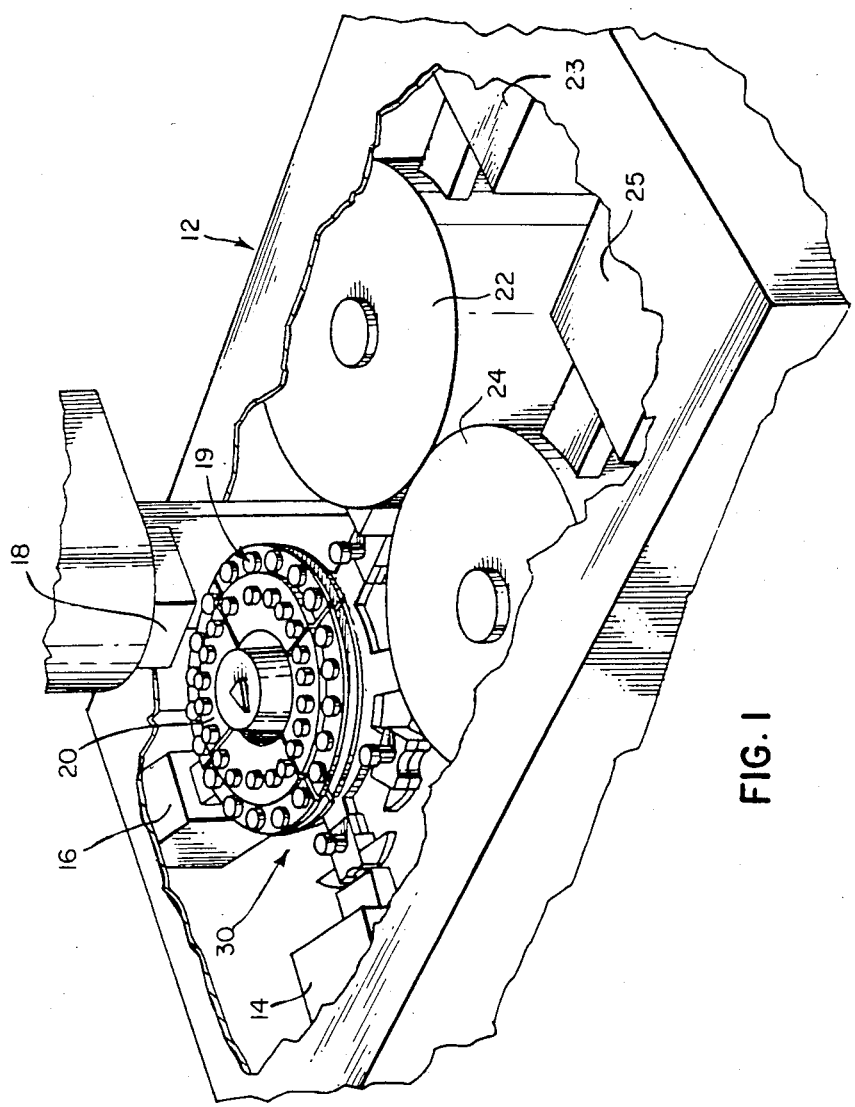
FIG. 1 is a fragmentary perspective view of apparatus constructed to employ the instant invention, particularly as a clinical analyzer.

An analyzer 12 such as that shown in FIG. 1 comprises two supply units 14 and 16 that feed or supply test elements to distributor means 30 to distribute or move the elements to the various stations 18, 22 and/or 24. One of the units 14 and 16 supplies colorimetric test units, that is, those that detect the analyte concentration by a colorimetric reaction, and the other unit 14 or 16 supplies potentiometric test elements. Station 18 is the liquid dispensing station, discussed in detail hereinafter. Stations 22 and 24 are the respective incubators for colorimetric and potentiometric test elements. Detection stations 23 and 25 provide means for detecting a change in the test element after the incubation period. Thus, one of stations 23 and 25 includes a photometer constructed for colorimetric detection and the other includes a potentiometer. The details of units 14, 16, incubators 22, 24, detector stations 23, 25, and distributor 30 are well known and are not critical. Useful examples of distributor 30 appear in U.S. Pat. No. 4,296,070, issued Oct. 20, 1981. Examples of incubator 22 and associated test element handling means appear in, e.g., U.S. Pat. No. 4,298,571, issued on Nov. 3, 1981.

Figure 2:
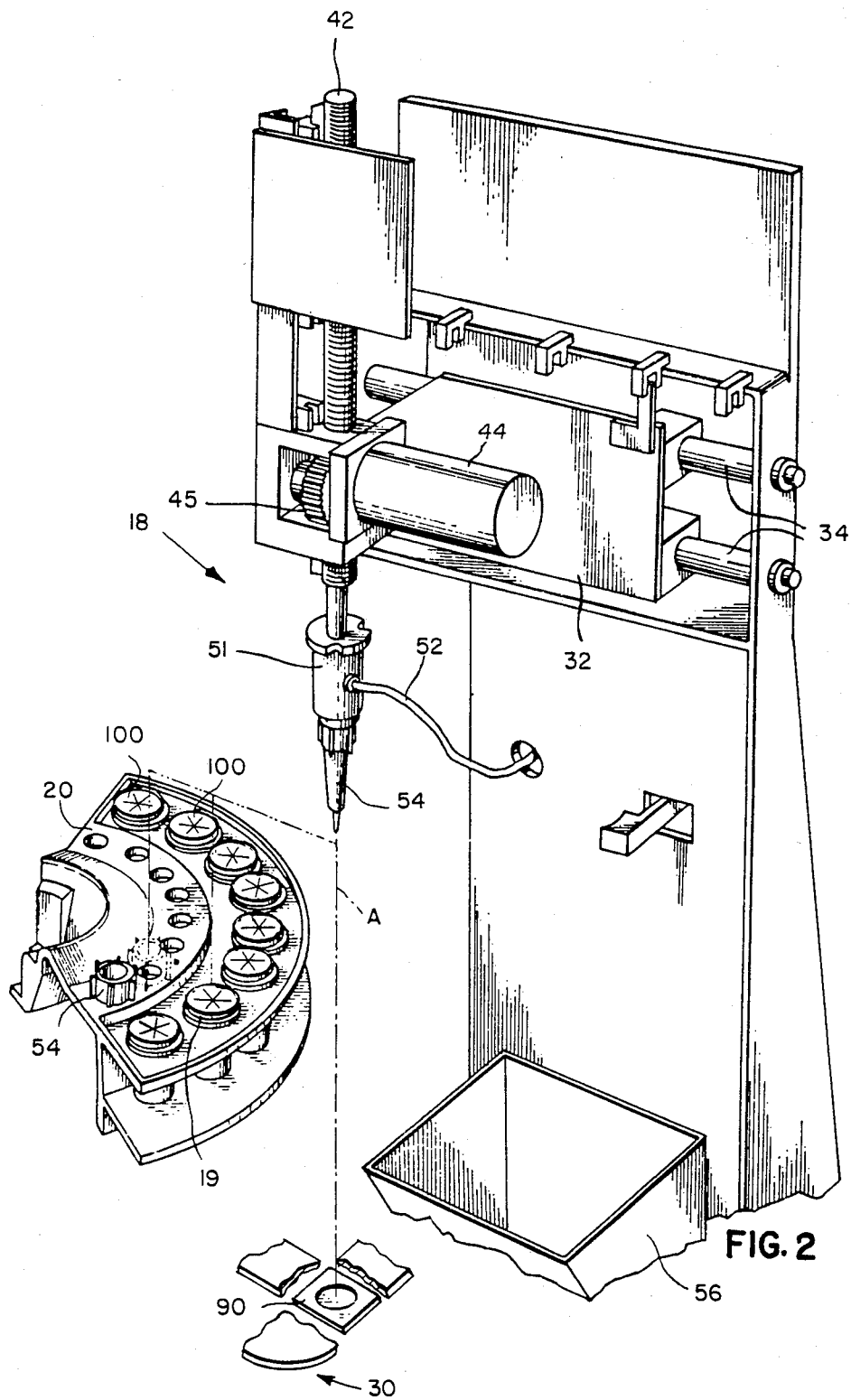
FIG. 2 is a fragmentary perspective view illustrating the aspirating and dispensing portion of the apparatus of FIG. 1.

The patient liquids are supplied to the analyzer in a plurality of separate containers 19, each having a cap 100 and each being supported in a tray 20 shaped as a quadrant of a circle, FIGS. 1 and 2. Trays 20 also supply a plurality of disposable tip storage units 54. Such units comprise a cylindrical body 56 that terminates in a dispensing end 58 connected to body 56 by a cone portion 60, FIG. 3. The containers 19 and the tips 54 are supported in respective apertures in the tray disposed as concentric arcs, the containers 19 preferably being disposed outside of the arc of tips 54. Trays 20 in turn are suitably rotated past liquid dispensing station 18. Station 18 comprises a vertically movable probe 51 on which tips 54 fit, one at a time. Probe 51 is raised and lowered by a screw 42 and pinion 45, such pinion being driven by a motor 44. Shaft 42 is mounted on a frame 32 that is slidably oscillated so as to move probe 51 and tip 54 through vertical plane A that extends out over and intercepts the two arcs in tray 20 along a radius thereof. Frame 32 moves on rails 34, in response to automated commands from a microprocessor, not shown. Aspirating vacuum and dispensing pressure are supplied to probe 51 and thence to tip 54 by a pressure line 52. Further details of such a dispensing station are given in the aforesaid U.S. Pat. No. 4,287,155, the details of which are hereby incorporated by reference. The dispensing sequence, as described in the '155 patent, is that probe 51 picks up one of the tips 54 from tray 20, pushes through the cap of the container 19 aligned in plane A, aspirates the liquid, is withdrawn from container 19, and then moves over a test element 90 positioned by distributor 30 as shown for dispensing the liquid onto the test element. Thereafter the tip 54 is discarded into waste disposable bin 56, and test element 90 is inserted into one of the incubators.

In accord with one aspect of the invention, and particularly referring to FIG. 3, a cap stripper 110 is provided for holding down cap 100 and container 19 against tray 20 each time one of the containers is moved into plane A for the aspiration step. Such stripper comprises arms 112 and 114 extending from the apparatus housing in a manner providing a fixed reference plane, and a dowl 116 slidably mounted within aperture 118 in each of the arms. Cotter pins 120 or the like are used to keep the dowls from falling out of their arms. Each dowl is seated on an end of a D-shaped camming member 130 comprising, FIGS. 3 and 4, two strips 132, 134 joined together at opposite end portions 136 and 138 to which dowls 116 are attached. Strips 132 and 134 are separated a distance sufficient to allow probe 51 to carry tip 54 down between them, FIG. 4. To bias the strips 132 and 134 downwardly, compression springs 140 are mounted between portions 136 and 138 and the respective reference arms 112 and 114. The downward bias of the strips accommodates variances in the height of the caps 100 and/or in the height of containers 19.

Arms 112 and 114 are either permanently fixed against vertical movement, or alternatively, are mounted to a hood, not shown, that is fixed in place over the dispensing station 18 during dispensing but which pivots out of the way, along with stripper 110, when trays 20 are loaded or unloaded. In either case, the camming member 130 remains in place to hold down the caps against the tray surface, for a plurality of sequentially advanced containers.

As is readily apparent, the use of stripper 110 is as follows—a capped container 19 is moved into position in plane A along the direction indicated by arrow 150, and as it does, cap 100 is cammed against its reference surface, tray 20, by reason of the sloped portion of strips 132 and 134. This in turn raises the strip (arrows 160) from the dotted position to that shown in solid, against the action of springs 140. Tip 54 is then pushed through cap 100, the latter having been scored as shown in FIG. 5 along lines 200 that form teeth 210. As shown in FIG. 3 teeth 210 tend to bind against tip 54. When tip 54 is withdrawn from both container 19 and its liquid, after aspiration, cap 100 is held by stripper 110 against container 19 and surface 20, and is prevented from following the upward movement of the withdrawing tip. As a result, the withdrawal of the exterior surface of tip 54 (a) from the liquid and (b) through the teeth 210 is maintained at a relatively slow and uniform rate. The withdrawal of the tip from the liquid and the cap at this relatively slow, uniform rate of withdrawal has been shown to be important in the reduction in the number of instances of perfusion, by a mechanism that is not clearly understood.

Alternatively, the stripper of FIG. 3 is useful even if it contacts the cap only for the withdrawal movement of tip 54. That is, strips 132 and 134 need not be placed in contact with cap 100 until just prior to the withdrawal movement of tip 54 from its aspirating position. To that end, arms 112 and 114 can be mounted, not shown, for movement into the position shown in FIG. 3 only just before the withdrawal movement of probe 51 and tip 54. Stripper 110 is of course retained in such position during the entire withdrawal movement of the probe and tip.

Another embodiment of the stripper is shown in FIGS. 6-9, wherein the cap stripper is moved into and away from its stripping position depending upon the position of the aspirating probe. Parts similar to those previously described bear the same reference numeral to which the distinguishing suffix "a" has been appended. Thus, containers with caps 100a are mounted in trays 20a for rotation past dispensing station 18a and under probe 51a carrying disposable tip 54a, as in the previously described embodiment. The frame at dispensing stations 18a includes a fixed vertical plate 300 cut away at 301, FIG. 6, to allow probe 51a to move in plane A out over trays 20a, and back to a position above the test element, not shown, awaiting the liquid from tip 54a.

Figure 6:
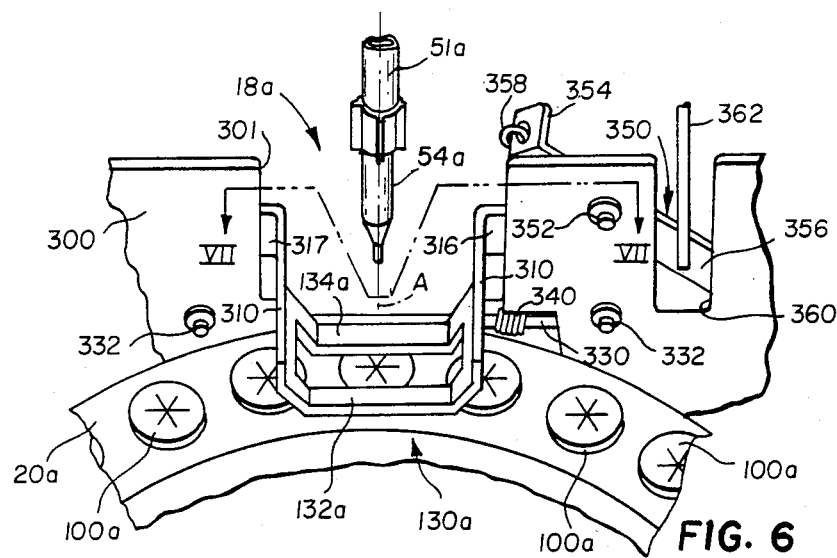
FIG. 6 is a fragmentary perspective frontal view of another embodiment of the invention.
Figure 8:
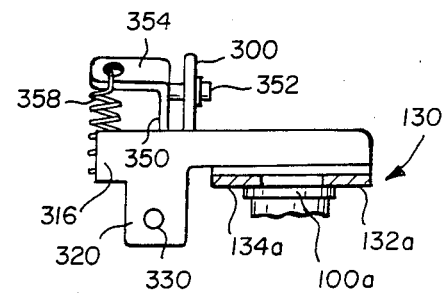
FIG. 8 is a fragmentary sectional view taken along the line VIII—VIII of FIG. 7 with a fragment of a capped container added for clarity.
Figure 9:
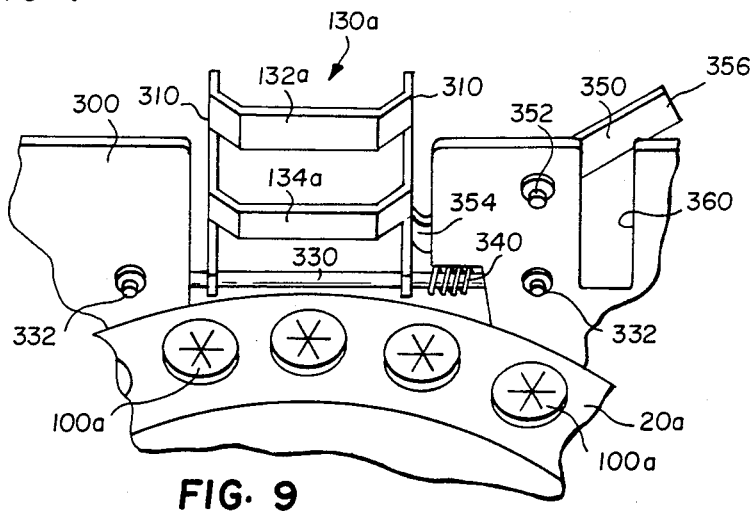
FIG. 9 is a fragmentary perspective view similar to that of FIG. 6, but with the parts in their alternate position.

In accordance with this embodiment, the stripper is pivotally mounted for movement centered on plane A, from a position in which the stripper is horizontally disposed to hold down a capped container in place for aspiration, FIG. 6, to another position, FIG. 9, in which it is vertically disposed out of the way for movement of tray 20a. More specifically, the stripper comprises a camming member 130a, FIGS. 6-8, welded to two arms 310 adjacent ends 312 of such arms, FIG. 7. Member 130a itself comprises two strips 132a and 134a. The opposite ends of arms 310 are bent outwardly to form ears 316, 317 that extend behind frame 300, FIGS. 6 and 7. Mounting lugs 320 extend downwardly from the underside of arms 310, FIG. 8, to journal camming member 130a to a pivot rod 330 fixed to frame 300 by screws 332.

Figure 7:
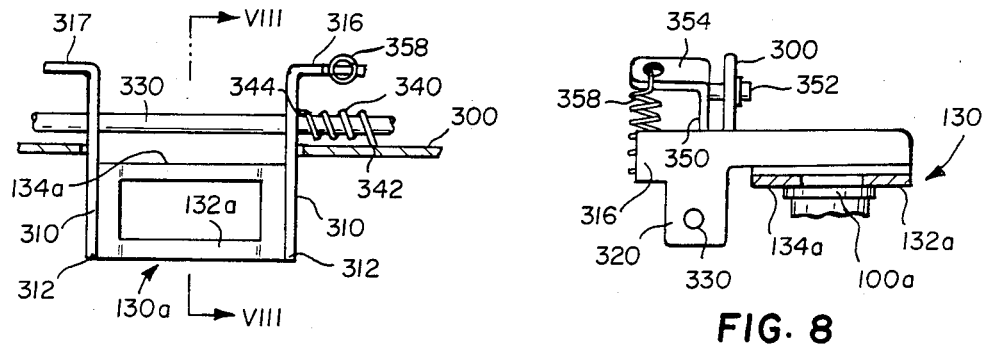
FIG. 7 is a fragmentary sectional view taken horizontally generally through the line VII—VII shown as extending across the front surface of plate 300, FIG. 6, caps 100a, tray 20a and lever 350 having been omitted for clarity.

To bias camming member 130a upwardly as shown in FIG. 9, a torsion spring 340 is mounted on rod 330 with one end 342 affixed to the back of frame 300, FIG. 7. The other end 344 of spring 340 is secured to the adjacent arm 310. Thus, as camming member 130a moves downwardly from the vertical position shown in FIG. 9 to that shown in FIG. 6, spring 340 is forced to wind up even further, thus tending to force camming member 130a back to its vertical position.

To forcing camming member 130a downward against the action of spring 340, lever 350 is pivotally mounted on the back of frame 300, FIGS. 6 and 8, by a pivot screw 352. One end 354 of lever 350 is apertured to receive one end of a tension spring 358 attached to ear 316 of arm 310, FIGS. 6-8. The opposite end 356 of lever 350 extends into a position behind a slot 360 cut away in frame 300 for the movement of a trip arm 362. Trip arm 362 is in turn mounted to be cammed downwardly as probe 51a is moved downwardly, thus forcing lever 350 to move clockwise from its position shown in FIG. 9, with end 356 raised, to that position shown in FIG. 6 wherein end 356 is lowered. End 354 is thus raised and spring 358 is extended so as to pull against ear 316. The spring constants of springs 340 and 358 are selected so that spring 358 overcomes the bias of spring 340, forcing arms 310 to pivot downwardly and thus to cam the positioned cap 19a and container against tray 20a.

It will be readily apparent that the flexure of springs 340 and 358 allows camming member 130a to accommodate variations in the heights of caps 100a or their containers. In addition, spring 358 is sufficiently flexible as to allow trip arm 362 to depress lever 350 well beyond the point at which stripping means 130a is fully pressed against the cap to be pierced. Such overtravel of arm 362 and lever 350 is preferred, so that when probe 51a, and thus trip arm 362, begin to withdraw from the capped container, spring 358 will still have enough residual tension as to hold down camming member 132a against cap 100a while tip 54a is being withdrawn by the probe. Thus, camming member 132a does move away from the caps and the tray 20a with each withdrawal of probe 51a for dispensing but only after tip 54a has been fully disengaged from the cap.

The invention has been described in detail with particular reference to preferred embodiments thereof, but it will be understood that variations and modifications can be effected within the spirit and scope of the invention.

What is claimed is:

1. In apparatus for measuring the concentration of analytes in a liquid deposited onto a test element, such liquid being drawn from a quantity in a container covered by a pierceable cap, the apparatus comprising means for aspirating such liquid from said container into a storage unit constructed to receive and dispense such liquid, means for moving said unit: (i) from a location outside of the container, into an aspirating position in which such cap is pierced by such storage unit and said unit is immersed in the liquid in such container, and (ii) away from said aspirating position, stripping means for stripping the pierced cap off the storage unit, means for dispensing at least a fraction of such liquid out of the storage unit onto such test elements, and means for detecting a change in such test element that is indicative of the amount of such analytes present in the liquid, the improvement wherein said stripping means includes means for holding such container during the entire movement of said storage unit away from said aspirating position therein, to prevent non-uniform relative movement between the storage unit and the container such as could cause perfusion during subsequent dispensing.

2. In apparatus for transferring liquid from a container covered by a pierceable cap, to analysis means for analyzing the liquid, such apparatus including means for aspirating such liquid from said container into a storage unit constructed to receive and dispense such liquid, means for moving said unit: (i) from a location outside of the container into an aspirating position in which such cap is pierced by such storage unit and said unit is immersed in the liquid in such container, and (ii) away from said aspirating position, stripping means for stripping the pierced cap off the storage unit, and means for dispensing at least a fraction of such liquid out of the storage unit onto such analysis means, the improvement where said stripping means includes means for holding such container during the entire movement of said storage unit away from said aspirating position therein, to prevent non-uniform relative movement between the storage unit and the container such as could cause perfusion during subsequent metering.

3. Apparatus as defined in claim 1 or 2, and further including means for mounting said holding means relative to a fixed surface to accommodate variations in thickness of said containers and caps.

4. Apparatus as defined in claim 3, wherein said mounting means include means for biasing said holding means toward said fixed surface, whereby said container is held against said fixed surface during said entire movement, by the action of said holding means.

5. Apparatus as defined in claim 1 or 2, wherein said stripping means is mounted to remain in position for holding each said cap and container against said fixed surface, for a plurality of sequential containers.

6. Apparatus as defined in claim 1 or 2, wherein said stripping means is mounted to move away from said fixed surface when said storage unit becomes fully disengaged from the stripped cap.

* * * * *